(12) United States Patent
Mori et al.

(10) Patent No.: US 8,594,401 B2
(45) Date of Patent: Nov. 26, 2013

(54) AUTOMATED CHARACTERIZATION OF TIME-DEPENDENT TISSUE CHANGE

(75) Inventors: Susumu Mori, Ellicott City, MD (US); Michael I. Miller, Towson, MD (US)

(73) Assignee: The Johns Hopkins University, Baltimore, MD (US)

(*) Notice: Subject to any disclaimer, the term of this patent is extended or adjusted under 35 U.S.C. 154(b) by 290 days.

(21) Appl. No.: 13/075,408

(22) Filed: Mar. 30, 2011

(65) Prior Publication Data

US 2011/0274330 A1    Nov. 10, 2011

Related U.S. Application Data

(60) Provisional application No. 61/319,043, filed on Mar. 30, 2010.

(51) Int. Cl.
*G06K 9/00* (2006.01)

(52) U.S. Cl.
USPC .................................................... 382/128

(58) Field of Classification Search
USPC ................... 382/128, 131, 132, 294
See application file for complete search history.

(56) References Cited

U.S. PATENT DOCUMENTS

| | | | | |
|---|---|---|---|---|
| 7,616,783 | B2 * | 11/2009 | Valadez | 382/107 |
| 7,738,683 | B2 * | 6/2010 | Cahill et al. | 382/128 |
| 2009/0046951 | A1 * | 2/2009 | Paragios et al. | 382/294 |
| 2009/0129650 | A1 * | 5/2009 | Hawkes et al. | 382/131 |
| 2011/0235884 | A1 * | 9/2011 | Schreibmann et al. | 382/131 |

OTHER PUBLICATIONS

Beg et al., "Computing Large Deformation Metric Mappings via Geodesic Flows of Diffeomorphisms," 2005, International Journal of Computer Vision 61(2), pp. 139-157.
Gao et al., "Computer-Assisted Quantitative Evaluation of Therapeutic Responses for Lymphoma Using Serial PET/CT Imaging," 2010, Acad. Radiol. 17, pp. 479-488.
X. Li, H. Jiang, and S. Mori, Johns Hopkins University, www.mristudio.org, <last accessed May 10, 2011.>.
Granander and Miller, Statistical Computing & Statistical Graphics Newsletter, vol. 7, No. 3, Dec. 1996, pp. 3-8.

* cited by examiner

*Primary Examiner* — Tom Y Lu
(74) *Attorney, Agent, or Firm* — Venable LLP; Henry J. Daley; Christopher B. Tokarczyk

(57) ABSTRACT

A non-invasive medical imaging system includes: an imaging scanner capable of generating an imaging signal from a subject under observation inside the imaging scanner; a signal processing system in communication with the imaging scanner, and a data storage unit in communication with the signal processing system, wherein the data storage unit is suitable for storing a first image corresponding to a tissue region of the subject, wherein the signal processing system is capable of generating a second image encoding the tissue region of the subject by performing a reconstruction based on the imaging signal, the imaging signal acquired at a later time than the first image; wherein the signal processing system is constructed to receive the imaging signal from the imaging scanner and the first image from the data storage unit respectively, wherein the signal processing system is adapted to provide a registered first image by registering the first image to the second image via a transformation in a space of diffeomorphism, wherein the signal processing system is further adapted to compute a difference image between the second image and the registered first image; and wherein the signal processing system is further adapted to output the difference image.

20 Claims, 17 Drawing Sheets

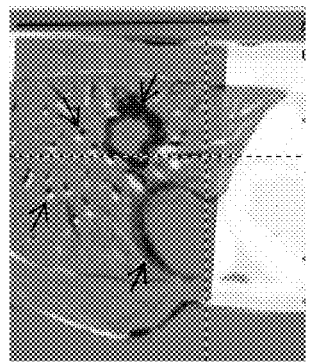
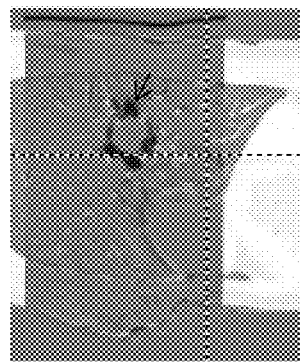
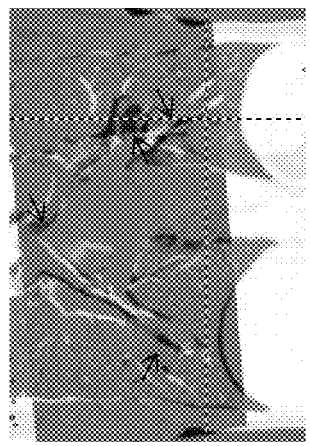
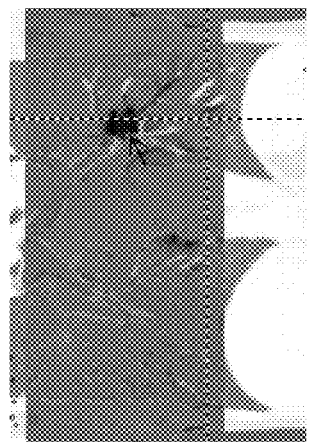
FIG. 4C
FIG. 4D
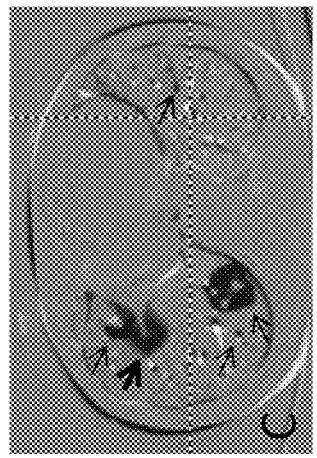
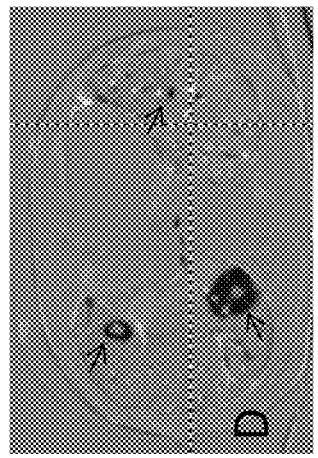

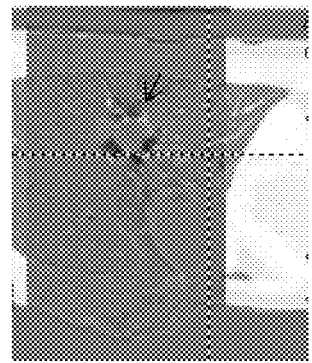
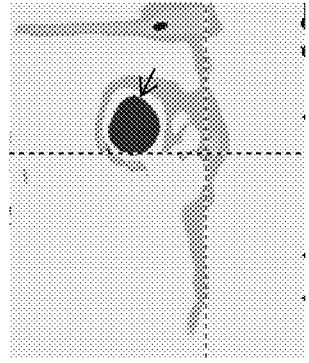
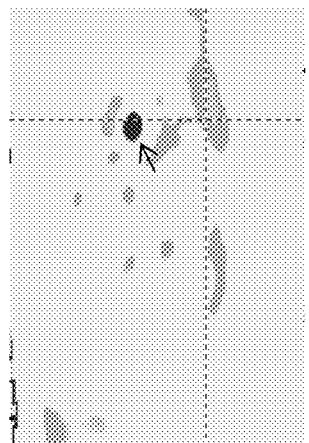
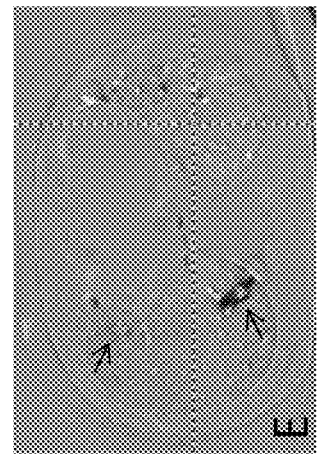
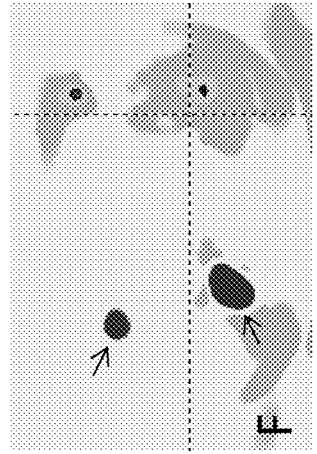
FIG. 4E
FIG. 4F

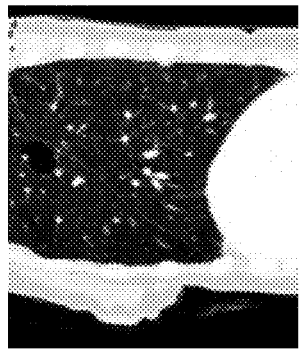
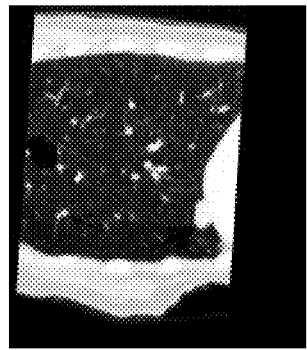
FIG. 5A
FIG. 5B

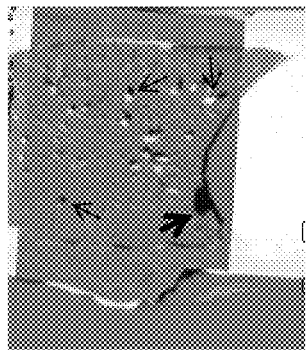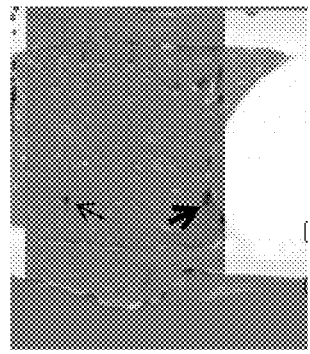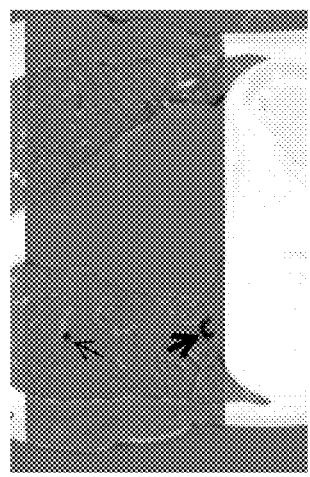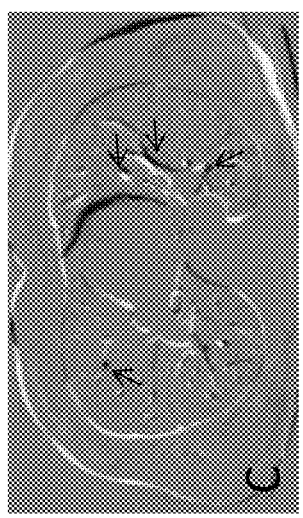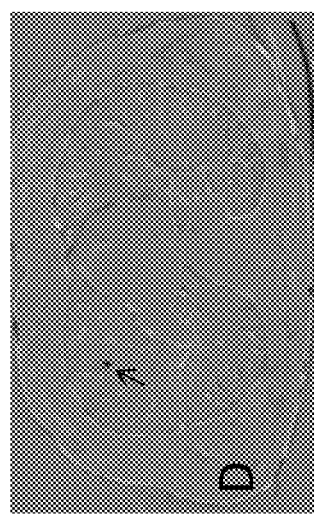
FIG. 5C  FIG. 5D

AUTOMATED CHARACTERIZATION OF TIME-DEPENDENT TISSUE CHANGE

CROSS-REFERENCE OF RELATED APPLICATION

This application claims priority to U.S. Provisional Application No. 61/319,043 filed Mar. 30, 2010, the entire contents of which are hereby incorporated by reference.

The U.S. Government has a paid-up license in this invention and the right in limited circumstances to require the patent owner to license others on reasonable terms as provided for by the terms of Grants No. P41 RR15241 awarded by the National Institute of Health.

BACKGROUND

1. Field of Invention

The current invention relates to systems and methods for computer-aided detection and quantification of soft tissue changes.

2. Discussion of Related Art

The recent advent of modern radiological imaging devices leads to an overwhelming amount of anatomical information, which often exceeds the ability of radiologists to inspect within a short enough period of time. For example, a modern multi-detector row CT (MDCT) can produce images of the entire torso with 1 mm resolution within a few seconds, which comprises hundreds of axial slices. For detection and monitoring of a tumor, MDCT is often repeated during the course of therapy, which further multiplies the amount of anatomical information. Characterization of growth or shrinkage of tumor masses, as well as identification of metastasis, are an essential part of CT-based diagnosis. Computer-aided detection and quantification of time-dependent anatomical changes are, therefore, highly desirable. The automated detection of tissue shape change is conceptually straightforward; images from two time points can be three-dimensionally registered and a subtraction image can be generated. However, the vast majority of our organs are highly deformable and the registration could be challenging. Among the organs in our torso areas, the lung could be one of the simplest, and therefore most researched organs for such automated detection of anatomical changes. Nonetheless, precise registration of the soft tissue organs remains a challenge, especially for those organs that have undergone substantial shape changes. Thus, there is a need in the art to take advantage of the recent progress in radiological imaging devices and improve the quality of computer-aided detection and quantification of time-dependent anatomical changes.

SUMMARY

An embodiment of the present invention provides a non-invasive medical imaging system, including: an imaging scanner capable of generating an imaging signal from a subject under observation inside the imaging scanner; a signal processing system in communication with the imaging scanner, and a data storage unit in communication with the signal processing system, wherein the data storage unit is suitable to store a first image corresponding to a tissue region of the subject, wherein the signal processing system is capable of generating a second image encoding the tissue region of the subject by performing a reconstruction based on the imaging signal; the imaging signal acquired at a later time than the first image; wherein the signal processing system is constructed to receive the imaging signal from the imaging scanner and the first image from the data storage unit respectively, wherein the signal processing system is adapted to provide a registered first image by registering the first image to the second image via a transformation in a space of diffeomorphism, wherein the signal processing system is further adapted to compute a difference image between the second image and the registered first image; and wherein the signal processing system is further adapted to output the difference image.

Another embodiment of the present invention may include a workstation, including: a receiving engine constructed to receive a first image and a second image of a subject; a registration engine constructed to provide a registered first image by registering the first image to the second image via a transformation in a space of diffeomorphism, the transformation having a corresponding quantity representing characteristic spatial effects of the transformation; and a difference engine constructed to compute a difference image between the second image and the registered first image of the subject.

Some embodiments of the present invention may provide a method for automatically tracking a time-dependent tissue change, including: obtaining a first radiographic image of a subject under observation; obtaining a second radiographic image of the subject at a later time; wherein the first and second radiographic images comprise a common region of interest of the subject; providing a registered image by registering the first radiographic image to the second image via a transformation in a space of diffeomorphism, wherein the transformation has a corresponding quantity indicating characteristic spatial effects of the transformation; obtaining a difference image between the second radiographic image and the registered first radiographic image; and outputting both the corresponding quantity and the difference image.

BRIEF DESCRIPTION OF THE DRAWINGS

Further objectives and advantages will become apparent from a consideration of the description, drawings, and examples.

FIG. 4C shows the subtraction images after the CT images of FIG. 4A have been registered to the CT images of FIG. 4B via a linear transformation.

FIG. 4D shows the subtraction images after the CT images of FIG. 4A have been registered to the CT images of FIG. 4B via a LDDMM transformation with one iteration.

FIG. 4E shows the subtraction images after the CT images of FIG. 4A have been registered to the CT images of FIG. 4B via a LDDMM transformation with three iterations according to a cascading alpha approach.

FIG. 4F shows corresponding LDDMM transformation matrices as Jacobian maps in the axial, coronal, and sagittal orientations.

FIG. 5A shows the CT images of a growing nodule taken at a first time for a subject in axial, coronal, and sagittal orientations.

FIG. 5B shows the CT images of a growing nodule and a newly emerging nodule taken at a second time for the same subject in axial, coronal, and sagittal orientations.

FIG. 5C shows the subtraction images after the CT images of FIG. 5A have been registered to the CT images of FIG. 5B via a linear transformation.

FIG. 5D shows the subtraction images after the CT image of FIG. 5A have been registered to the CT images of FIG. 5B via a LDDMM transformation with one iteration.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited herein are incorporated by reference as if each had been individually incorporated.

Figure 1:
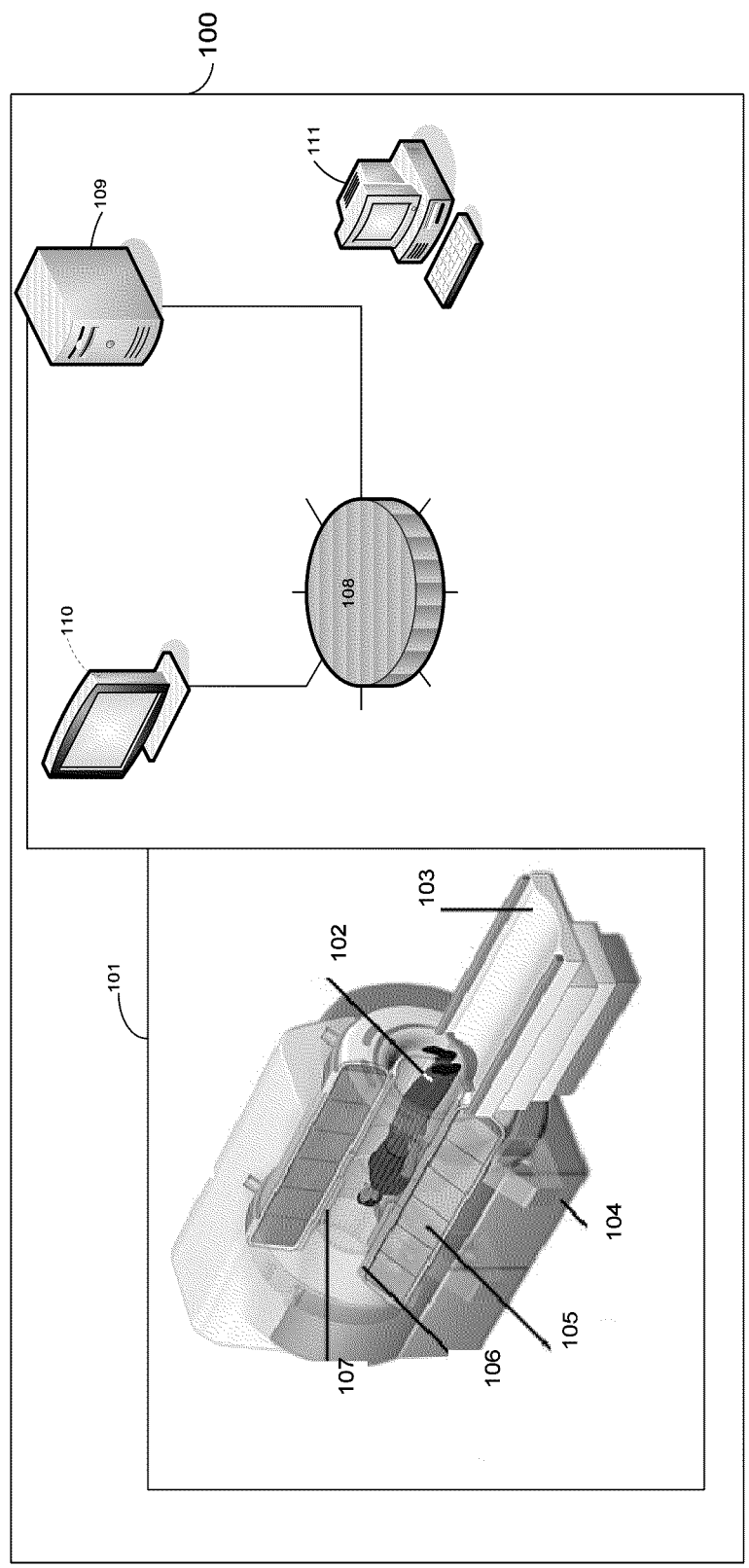
FIG. 1 is a schematic illustration of a non-invasive medical imaging system on which the embodiments of the current invention can be implemented.

FIG. 1 is a schematic illustration of a non-invasive medical imaging system on which an embodiment of the current invention can be implemented. The non-invasive medical imaging system 100 may include an imaging scanner 101 capable of generating an imaging signal encoding a tissue region of a subject 102 under observation on a patient table 103. The imaging scanner 101 may include a base 104 to be anchored to the floor of a scanning room, a bore area 105 to house transmitters 106 to emit energy into subject 102, and receivers 107 to detect an imaging signal from subject 102. The imaging scanner 101 may be a magnetic resonance imaging (MRI) scanner, a computed tomography (CT) scanner, a positron emission tomography (PET) scanner, a single photo emission computed tomography (SPECT) scanner, or an ultrasound scanner.

The non-invasive medical imaging system 100 may further include a data storage unit 108 and a signal processing system 109. The data storage unit 108 may be in communication with signal processing system 109 and may store a first image corresponding to a tissue region of the subject 102. The first image may be acquired at an earlier time than the imaging signal.

The signal processing system 109 may be in communication with the imaging scanner 101 to receive the imaging signal from the imaging scanner 101. The signal processing system 109 may be adapted to obtain a second image of the tissue region of the subject 102, for example, by performing a reconstruction based on the imaging signal. The reconstruction may be, for example, a filtered back projection.

Signal processing system 109 may be further adapted to register the first image to the second image via a transformation in a space of diffeomorphism. As discussed above, precise registration of the soft tissue remains a challenge for traditional approaches. To register two images from the same person, but with substantial shape changes, a highly elastic registration may be employed to accommodate the shape changes. In general, elastic registration could be readily trapped by a local minima, leading to non-biological severe transformation (e.g., negative Jacobian). For example, the lung has a certain biological topology with two lobes with air ducts that are supposed to be connected within a limit of image resolution. Local severe transformation can readily violate this biological topology, which would lead to disconnection of the ducts or connection of nearby ducts. In the abdominal area, the issue may be further complicated due to the substantial changes of intestine shapes.

To cope with severe local deformation, a low-dimensional non-linear transformation such as polynomial functions may be used, which may limit the quality of registration. A transformation in a space of diffeomorphism, however, may be better positioned to deal with tissue registration problems caused by severe local deformations. In particular, the connected structures may remain connected and disconnected structures remain disconnected even with severe local transformation. An example diffeomorphic transformation may be the Large Deformation Diffeomorphic Metric Mapping (LDDMM). LDDMM can keep the topology of the object while resulting in a high-dimensional nonlinear transformation. Like all transformations, each LDDMM transformation has a corresponding quantity, for example, the Jacobian map, indicating the characteristic spatial effects of the transformation.

Signal processing system 109 may be further adapted to compute a difference image between the second image and the registered first image, and to output the difference image or the corresponding quantity. The difference image may be output to a display device (for example, terminal 110 or console 111) or a printing device (for example, a thermo printer, a radiology resolution film printer, etc) for visualization. The difference image may be output to data storage unit 108 or another data storage unit in a digital format (e.g., DICOM) for record keeping.

Figure 2:
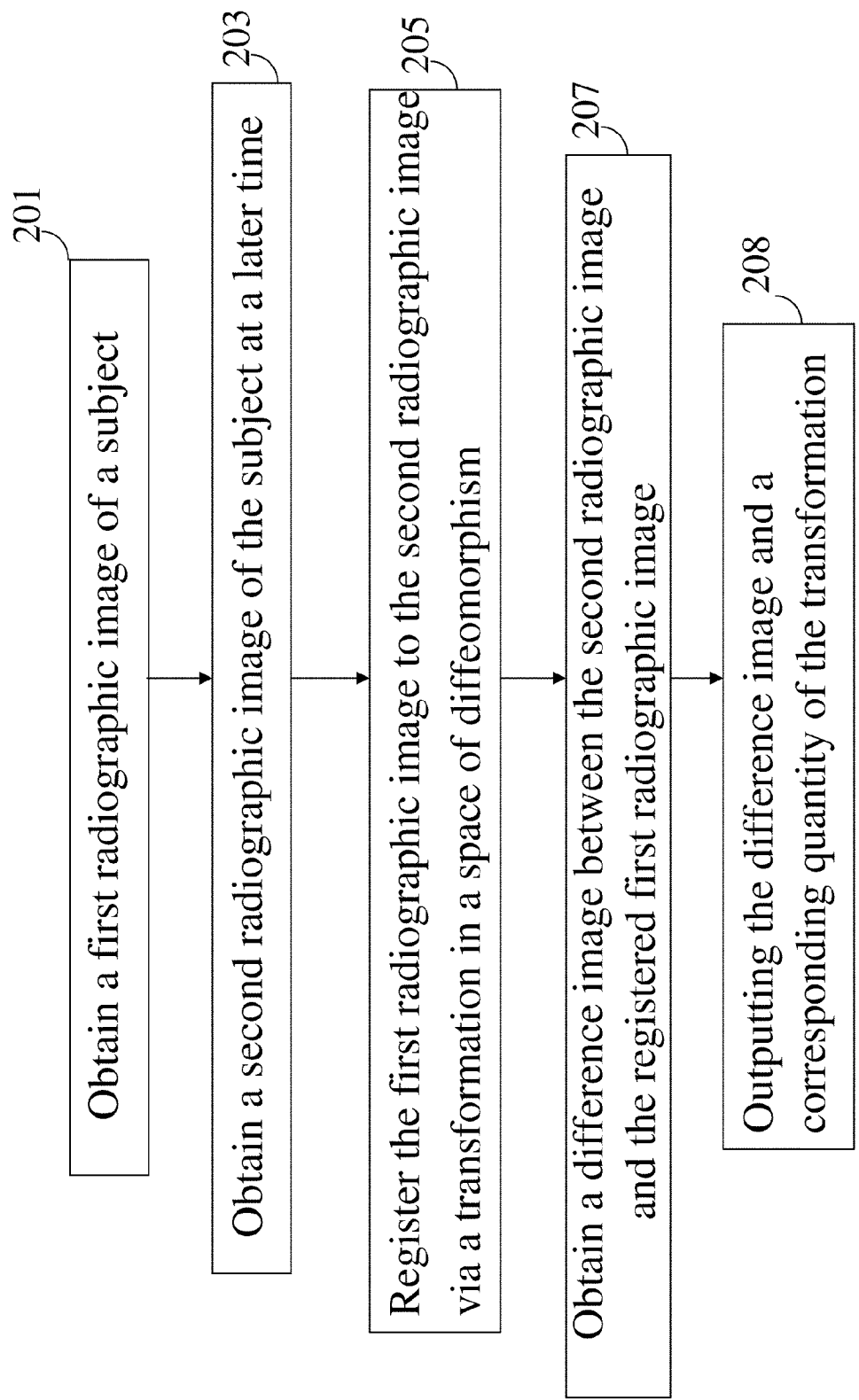
FIG. 2 is a flow-chart of a method according to some embodiments of the current invention.

FIG. 2 is a flow-chart of a method according to some embodiments of the current invention. In blocks 201 and 203, a first and second image of a subject under observation may be obtained, respectively. The second image may be obtained at a later time point than the first image. Both images may be radiographic images, such as, for example, an MRI image, a CT image, a PET image, a SPECT image, or an ultrasound image. Both the first and second radiographic images may comprise a common tissue region of the subject.

In block 205, the first radiographic image may be registered to the second image via a transformation in a space of diffeomorphism. The deformable template model of Granander (Granander and Miller, 1996) models the observed anatomical images, I, as an orbit under the group of transformations, G, acting on a template image, $I_0$, per Eq. (1).

$$I=GI_0=\{I_0\circ\phi^{-1},\phi\in G\} \quad (1)$$

Utilizing this model, for any given two images, $I_0$, $I_1$: $\Omega \subset R^3 \rightarrow R$, the LDDMM algorithm (Beg et al., 2003; Beg et al., 2005) calculates the diffeomorphic transformation, $\phi:\Omega\rightarrow\Omega$, registering the images such that $I_1=I_0\circ\phi^{-1}$. $\Omega \subset R^3$ is the 3D cube on which the data is defined. The optimal transformation, $\phi$, may be generated as the end point, $\hat\phi=\phi_1^v$, of the flow of smooth time-dependent vector field, $v_t\in V$, $t\in[0, 1]$, with the following ordinary differential equation, $$\frac{d\phi_t^v}{dt} = v_t(\phi_t^v), t \in [0, 1], \quad (2)$$

where $\phi_0$ is the identity transformation such that $\phi_0(x)=x$, $x\in\Omega$. Then, the optimal transformation, $\hat\phi$, is calculated by integrating the vector field that is found by minimizing the following equation.

$$\hat v = \underset{v:d\phi_t^v/dt=v_t(\phi_t^v)}{\operatorname{argmin}} \left(\int_0^1 \|v_t\|_v^2\, dt + \frac{1}{\sigma^2}\|I_0\cdot\varphi^{-1} - I_1\|_{L^2}^2\right). \quad (3)$$

The solution of Eq. (3) can be confined in the space of diffeomorphisms by enforcing smoothness on the vector fields, $v\in V$. The required smoothness may be enforced by defining the norm on V as $\|f\|_V=\|Lf\|_{L^2}$. L is a differential operator defined as $L=-\alpha\nabla^2+\gamma I_{3\times3}$, where $I_{3\times3}$ is the identity operator and $\nabla^2$ is the Laplacian operator $\|\cdot\|_{L^2}$ is the $L^2$ norm for the square integrable functions defined on $\Omega$. The gradient of the cost in Eq. (3) is:

$$\nabla_v E_t = 2v_t - K\left(\frac{2}{\sigma^2}|D\phi_{t,1}^v|\nabla J_t^0(J_t^0 - J_t^1)\right), \quad (4)$$

where the notation $\phi_{s,t}=\phi_s\circ\phi_t^{-1}$ is used.

In Eq. (4), $J_t^0=I_0\circ\phi_{t,0}$ and $J_t^1=I_1\cdot\phi_{t,1}\cdot|Df|$ is the determinant of the Jacobian matrix. $K:L_2(\Omega, R^3)\rightarrow V$ is a compact self-adjoint operator, defined by $\langle a,b\rangle_V = \langle Ka,b\rangle_v$, which satisfies $K(L^\dagger L)g=g$ for any smooth vector field $g\in V$. The parameter $\sigma$ may provide weighting between data matching and smoothness regularization terms.

A spatial transformation has a corresponding quantity that characterizes the spatial effects of the transformation. For the LDDMM transformation, the corresponding quantity can be the Jacobian map, in which the voxel with a Jacobian >1 may express an expansion and a Jacobian <1 may express the shrinkage.

In the LDDMM algorithm, Eq. (3) may be solved with a gradient descent algorithm using Eq. (4). In Eq. (4), the effect of the operator, $K=(L^\dagger L)^{-1}$, is low-pass filtering. The parameters $\alpha$ and $\gamma$ define the magnitude and frequency response of this filter. The ratio of $\alpha$ over $\gamma$ may be incrementally decreased when the LDDMM is repeated in an iterative manner. This application may provide additional fine tuning of the smoothness of the transformation. For example, according to a "cascading alpha" approach, in which the elasticity is gradually increased by empirically decreasing the ratio of $\alpha$ over $\gamma$, can be utilized to handle a large degree of shape differences properly.

In block 207, a difference image between the registered first image and the second image may be obtained. The difference image may be computed on a general purpose computer or a dedicated logic hardware.

In block 208, the difference image obtained in block 207 and the corresponding quantity of the transformation from block 205 may be output.

Using LDDMM to match the shapes of the two objects, a tool called DiffeoMap has been developed. This tool was applied to serial CTs of the lung and abdominal areas and the quality of the registration results were evaluated. FIG. 3 to FIG. 8 demonstrate the improvement in the quality of computer-aided detection and quantification of time dependent soft tissue changes by various embodiments of the present invention.

All CT examinations were performed with the same 64-slice multidetector CT scanner (Aquilion 64; Toshiba Medical Systems, Otawara, Japan). Images were acquired with 1- or 2-mm section thickness, 0.4-sec rotation time, beam pitch of 1.7 or 0.875, 120 kVp, and 300 mA per rotation. The reconstruction field of view was 320 mm for each section. The dose modulation protocol was not applied. CT scans were conducted after intravenous injection of 2 ml/kg of nonionic contrast medium (300 mg of iodine per milliliter) (Iomeprol, Eisai, Tokyo, Japan; Iopamidol, Nihon Schering, Osaka, Japan) at a rate of 3 ml/sec.

A cluster computer with 32 CPU and 128 GB of memory was used for LDDMM computation. The computation time varies depending on the size of the data. For 340×340×180 datasets, non-cascading LDDMM takes approximately one hour while the cascading LDDMM takes three times longer.

Figure 3C:
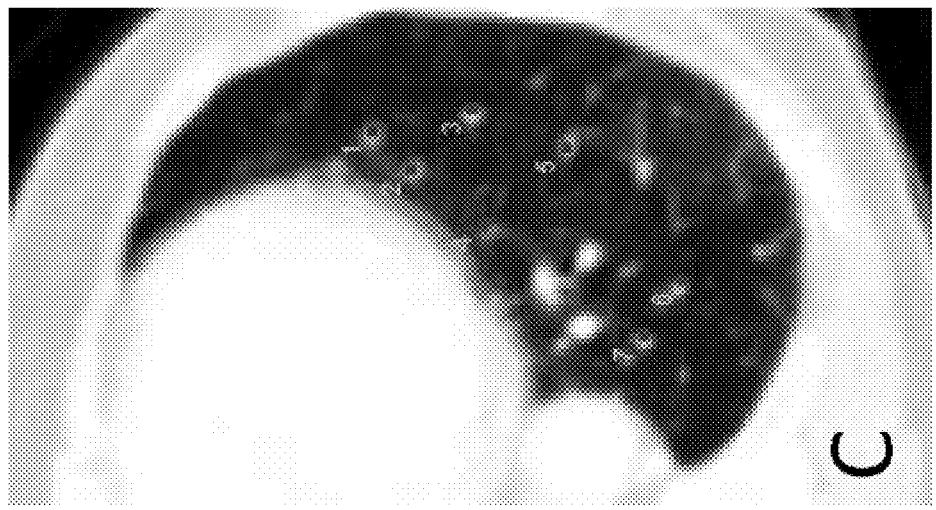
FIG. 3C shows the same landmarks transferred, via a LDDMM transformation, to the second CT image for both lobes of the same subject acquired at the second and later time point.
Figure 3B:
FIG. 3B shows the same landmarks transferred, via a linear transformation, to a second CT image for both lobes of the same subject acquired at the second and later time point.
Figure 3A:
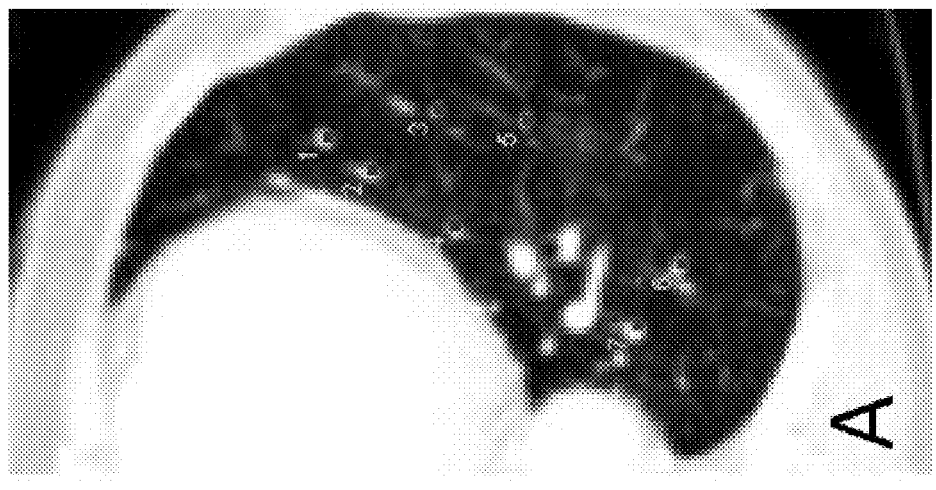
FIG. 3A shows landmarks placed at two axial and two sagittal levels on a first CT image for both lobes of the lungs of a subject acquired at the first time point.

To demonstrate the accuracies of registration by the linear and LDDMM transformation, landmark-based measurements were performed. FIG. 3A shows landmarks placed at two axial and two sagittal levels on a first CT image for both lobes of the lungs of a subject acquired at the first time point. Approximately 50 landmarks were defined in easy-to-define structures in the CT image at time point one. FIGS. 3B and 3C shows the same landmarks transferred, via a linear transformation and a LDDMM transformation, respectively, to a second CT image for both lobes of the same subject acquired at a second and later time point. To compensate for the mismatching between the transferred landmarks and the defined anatomy, manual corrections were performed. From the amount of manual translation to remap the landmarks, the registration accuracy was calibrated.

As shown in FIG. 3, linear registration often leads to gross misalignment of the structure. The landmark-based accuracy measurements were 3.0+/−2.0 and 0.8+/−0.6 mm, respectively, for the linear and the non-cascading LDDMM, while the registration error of the cascading LDDMM was within the measurement accuracy (99% of the landmarks did not have to repositioned). Thus, the superiority in registration accuracy resulting from the use of the differometric transform has been demonstrated.

FIG. 4 further demonstrates how the registration accuracy improves by using LDDMM with low elasticity and high elasticity using the cascading alpha approach described above.

Figure 4A:
FIGS. 4A and 4B show the CT images taken at a first and second times, respectively, for a subject in axial, coronal, and sagittal orientations.
Figure 4B:
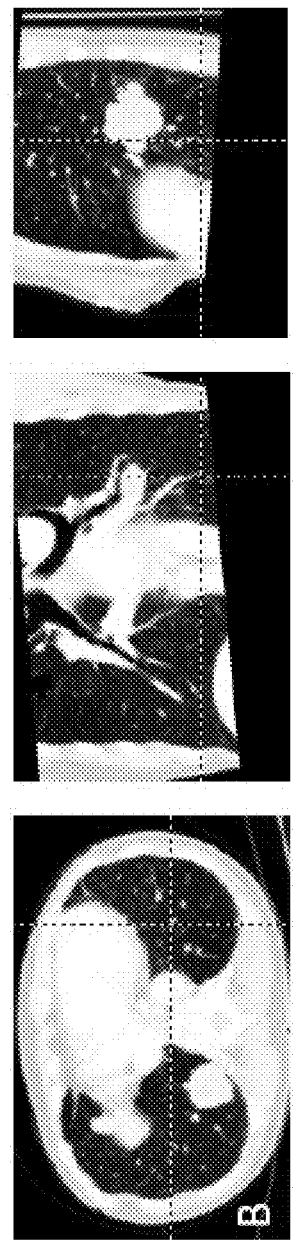

FIGS. 4A and 4B show the CT images taken at a first and second times, respectively, for a subject in axial, coronal, and sagittal orientations.

FIG. 4C shows the subtraction images after the CT images of FIG. 4A have been registered to the CT images of FIG. 4B via a linear transformation. The linear transformation delivers excellent registration for the overall anatomy but the subtraction image reveals numerous mismatching of fine lung structures. In this figure, growing nodules are indicated by white arrows while misaligned normal structures are shown by black arrows. Experienced readers could distinguish the growing nodules from the background misalignment using the typical appearance of misaligned structures (e.g. positive and negative subtraction artifacts adjacent each other or non-globular shapes). However, sometimes the background misalignment and growing nodule can be confusing as demonstrated by area indicated by the bold black arrow in the leftmost image of FIG. 4C.

FIG. 4D shows the subtraction images after the CT images of FIG. 4A have been registered to the CT images of FIG. 4B via a LDDMM transformation with one iteration. Compared to FIG. 4C, the first iteration of LDDMM with less elasticity can drastically improve the registration accuracy, thereby removing most of the misalignment artifacts. While the registration is still not perfect, the drastic decrease in misalignment artifacts should be translated to less burden for readers, effectively leads their attention to growing nodules.

FIG. 4E shows the subtraction images after the CT images of FIG. 4A have been registered to the CT images of FIG. 4B via a LDDMM transformation with three iterations according to the cascading alpha approach as described above.

As shown in FIG. 4E, with the iterations to increase local elasticity, the misalignment is almost completely removed. However, even the growing nodules may be transformed to the shape of the later time point, thereby erasing the interesting growth information in the subtracted images. In fact, if the transformation is perfect, the two images at different time points would become exactly the same, making the subtraction images virtually useless. Although this may seem a downside of highly elastic transformation, for such a "perfect" transformation, all information about anatomical differences may be stored in the transformation matrix that characterizes the spatial effects of the transformation. One way to retrieve relevant information, such as local nodule growth, may be to visualize the transformation matrix using a Jacobian map. FIG. 4F shows the corresponding LDDMM transformation matrices as Jacobian maps in the axial, coronal, and sagittal orientations for FIG. 4E. In this map, local growth is indicated by dark shade, effectively detection the growing nodules.

FIGS. 5A to 5F demonstrate how LDDMM can improve the detection and visualization of growing nodules. When a new nodule emerges due to metastasis, image-registration based analysis could react differently from growing nodules.

FIG. 5A shows the CT images of a growing nodule taken at a first time for a subject in axial, coronal, and sagittal orientations.

FIG. 5B shows the CT images of a growing nodule and a newly emerging nodule taken at a second time for the same subject in axial, coronal, and sagittal orientations.

FIG. 5C shows the subtraction images after the CT images of FIG. 5A have been registered to the CT images of FIG. 5B via a linear transformation.

FIG. 5D shows the subtraction images after the CT images of FIG. 5A have been registered to the CT images of FIG. 5B via a LDDMM transformation with one iteration.

Figure 5E:
FIG. 5E shows the subtraction images after the CT images of FIG. 5A have been registered to the CT images of FIG. 5B via a LDDMM transformation with three iterations according to the cascading alpha approach.
Figure 5E:
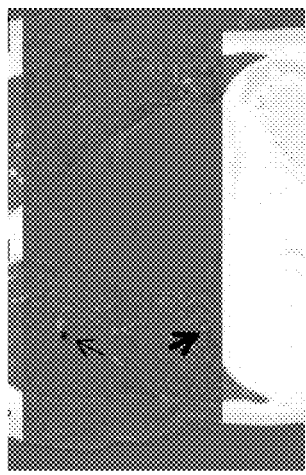
Figure 5E:
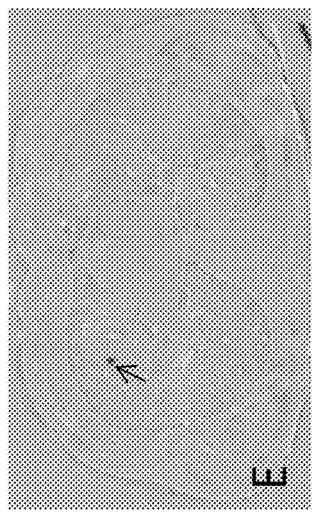

FIG. 5E shows the subtraction images after the CT images of FIG. 5A have been registered to the CT images of FIG. 5B via a LDDMM transformation with three iterations according to the cascading alpha approach.

A newly emerged nodule (indicated by white arrows) and a growing nodule (indicated by bold dark arrows) are captured in this patient. Similar to FIG. 4, there are many misalignment artifacts in the linearly registered images of FIG. 5C (indicated by black arrows), which largely disappear after the first iteration, as shown in FIG. 5D, and almost completely disappear using the cascading LDDMM, as shown in FIG. 5E.

Figure 5F:
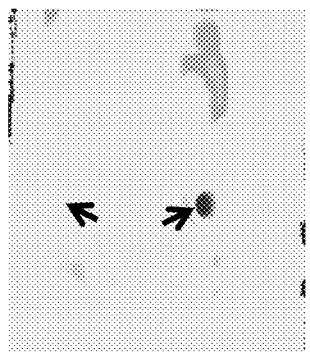
FIG. 5F shows corresponding LDDMM transformation matrices as Jacobian maps in the axial, coronal, and sagittal orientations.
Figure 5F:
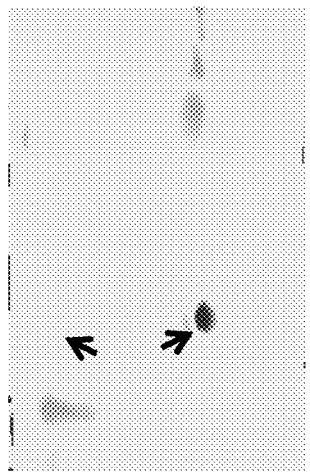
Figure 5F:
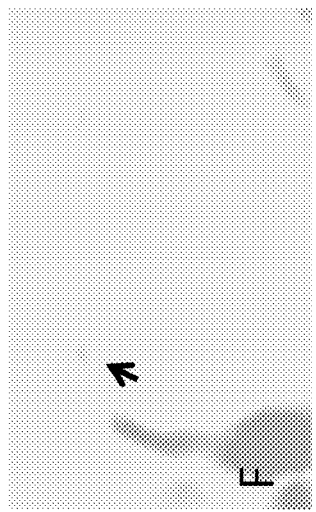
Figure 6A:
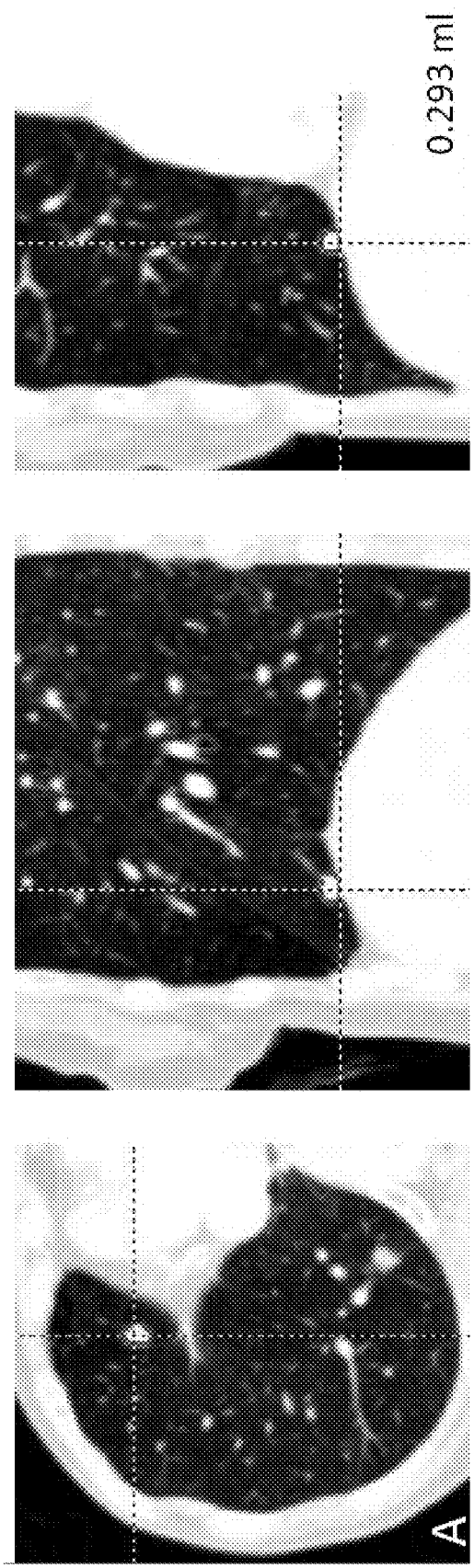
FIG. 6A shows the manual segmentation of a nodule at a first time point, yielding a volume measurement of 0.293 ml.
Figure 6B:
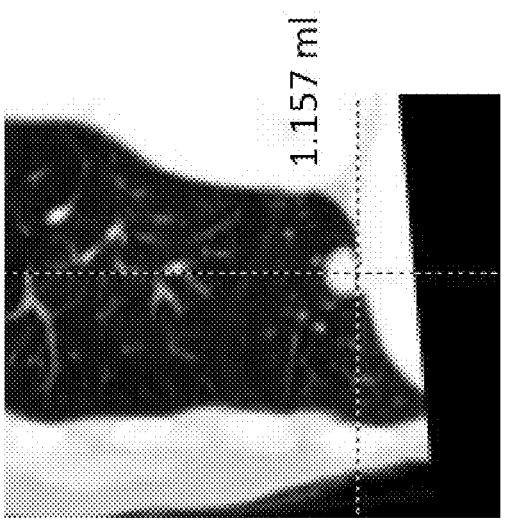
FIG. 6B shows the automatic delineation of the same nodule at a second and later time point by transferring the binary map of the manual segmentation of FIG. 6A to the CT images of FIG. 6B, yielding a volume measurement of 1.157 ml.
Figure 6B:
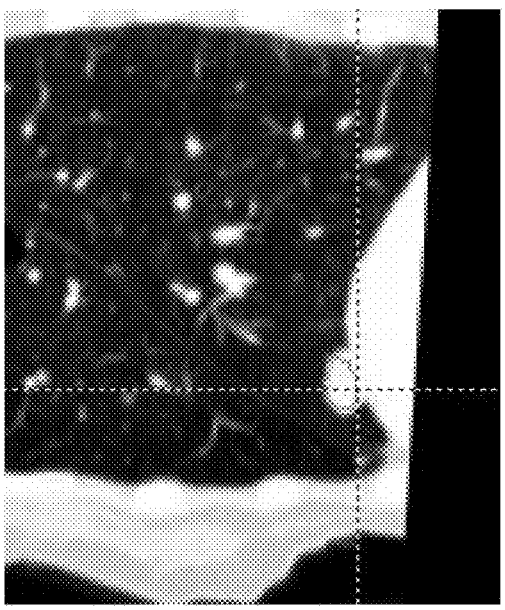
Figure 6B:
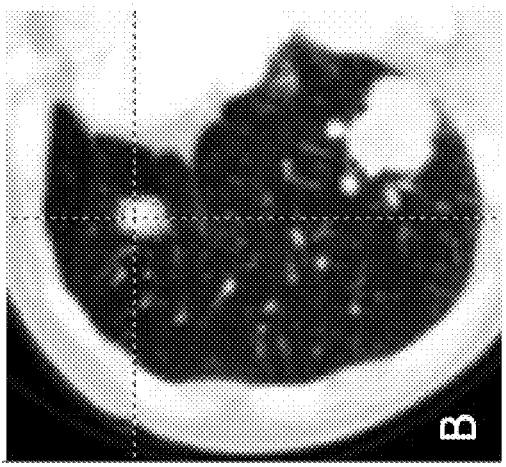

FIG. 5F shows the corresponding LDDMM transformation matrices as Jacobian maps in the axial, coronal, and sagittal orientations.

As demonstrated in FIG. 5, the growing nodule (indicated by bold dark arrows) also disappears from the subtraction image of FIG. 5E and appears as local expansion in the Jacobian map of FIG. 5F. However, the new nodule remains in the subtraction image and appears as non-existent in the Jacobian map because it cannot not be solved mathematically as a local growth. This feature demonstrates that both the subtraction image and the Jacobian map may be examined, after the LDDMM transformation, to enable differentiation of growing and appearing nodules.

In general, the detection of this small nodule could be extremely difficult on the subtraction image alone. Such detection may also be extremely difficult with linearly registered images having registration errors. In contrast, due to the high quality of registration, the cascading LDDMM may preserve most of the growth information as stored in the transformation matrix. Thus, the transformation matrix may be inspected during quantitative growth measurements of soft tissue changes over time.

FIG. 6 demonstrates one of the quantification approaches. FIG. 6A shows the manual segmentation of a nodule at a first time point, yielding a volume measurement of 0.293 ml. FIG. 6B shows the automatic delineation of the same nodule at a second and later time point by transferring the binary map of the manual segmentation of FIG. 6A to the CT images of FIG. 6B, yielding a volume measurement of 1.157 ml, which matches the volume measurement based on direct manual segmentation of the second time point. Thus, the nodule at the later time point may be automatically and accurately defined, from which the volume of the growing nodule at the second and later time can be retrieved. According to the same principle, a semi-automated method to measure nodule growth, as postulated in Gao (Gao, Xue et al. Computer-Assisted Quantitative Evaluation of Therapeutic Responses for Lymphoma Using Serial PET/CT Imaging." *Acad Radiol.*), may also be used to segment the soft tissue at the second time point.

Figure 7A:
FIG. 7A shows CT images in the axial and coronal orientations at the liver level for a subject at a first time point.

FIG. 7A shows CT images in the axial and coronal orientations at the liver level for a subject at a first time point.

Figure 7B:
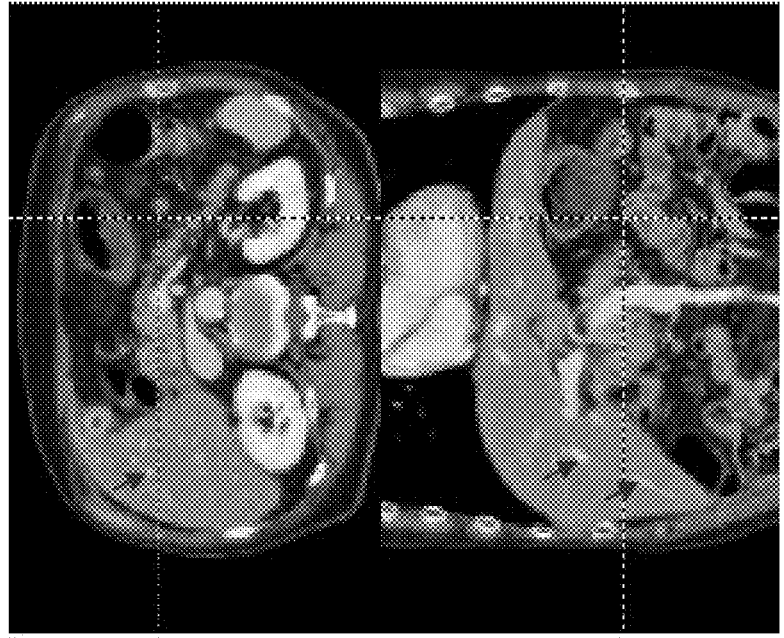
FIG. 7B shows CT images of FIG. 7A registered to the CT images of the same subject acquired at second and later time via a linear transformation, and a LDDMM.
Figure 7B:
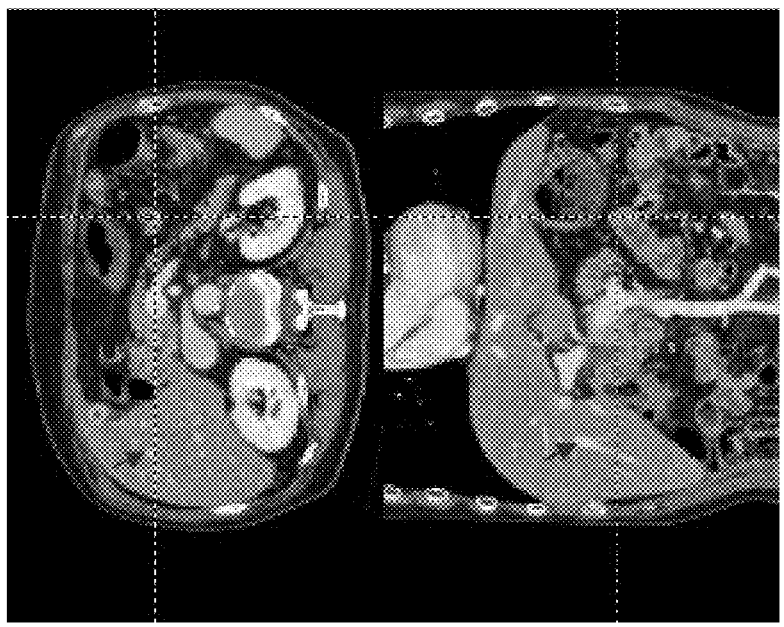

FIG. 7B shows CT images of FIG. 7A registered to the CT images of the same subject acquired at second and later time via a linear transformation and a LDDMM transformation.

Figure 7C:
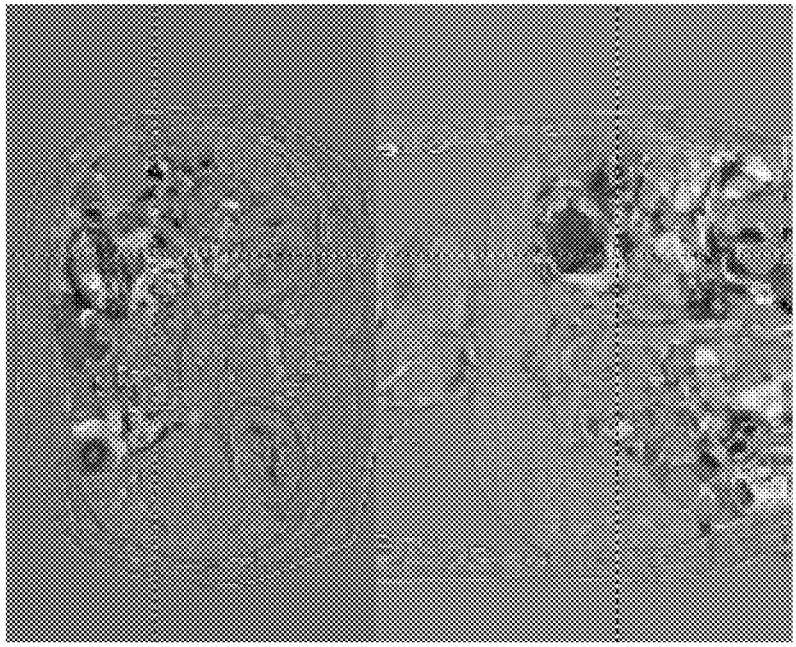
FIG. 7C shows the subtraction image after registration via the linear transformation and the LDDMM transformation.
Figure 7C:
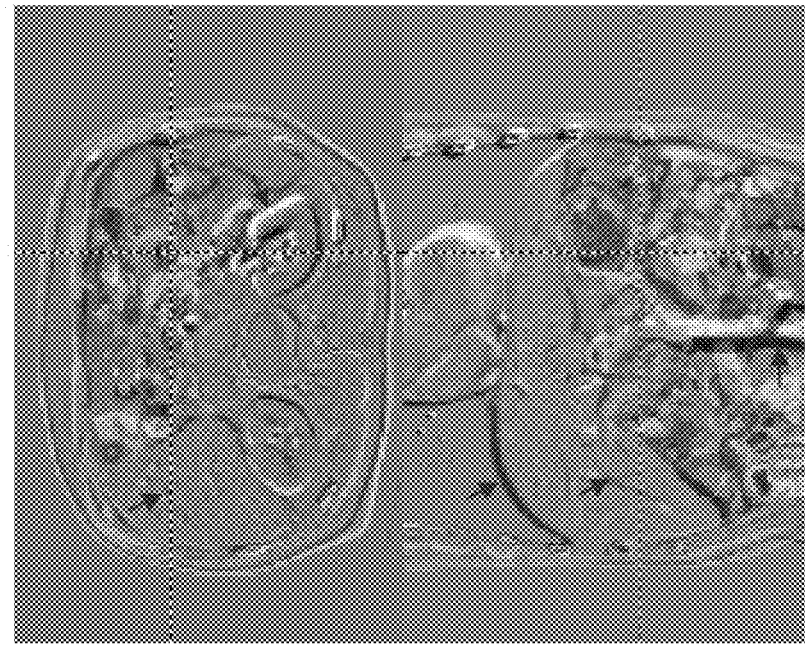

FIG. 7C shows the subtraction image after registration via the linear transformation and the LDDMM transformation. The arrows indicate structures that are misaligned by the linear transformation, but not by the LDDMM transformation.

Figure 8A:
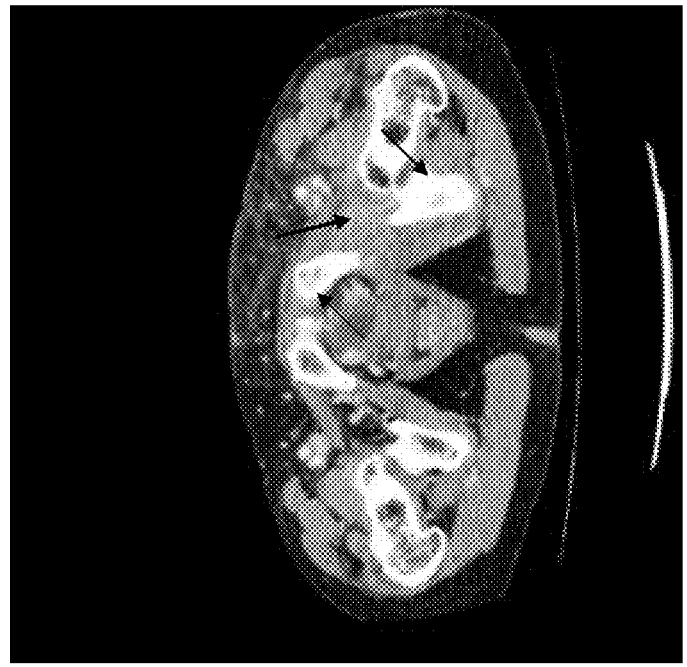
FIG. 8A shows CT images in the axial orientation at the groin level for a subject at a first and second time point.
Figure 8A:

FIG. 8A shows CT images in the axial orientation at the groin level for a subject at a first and second time point.

Figure 8B:
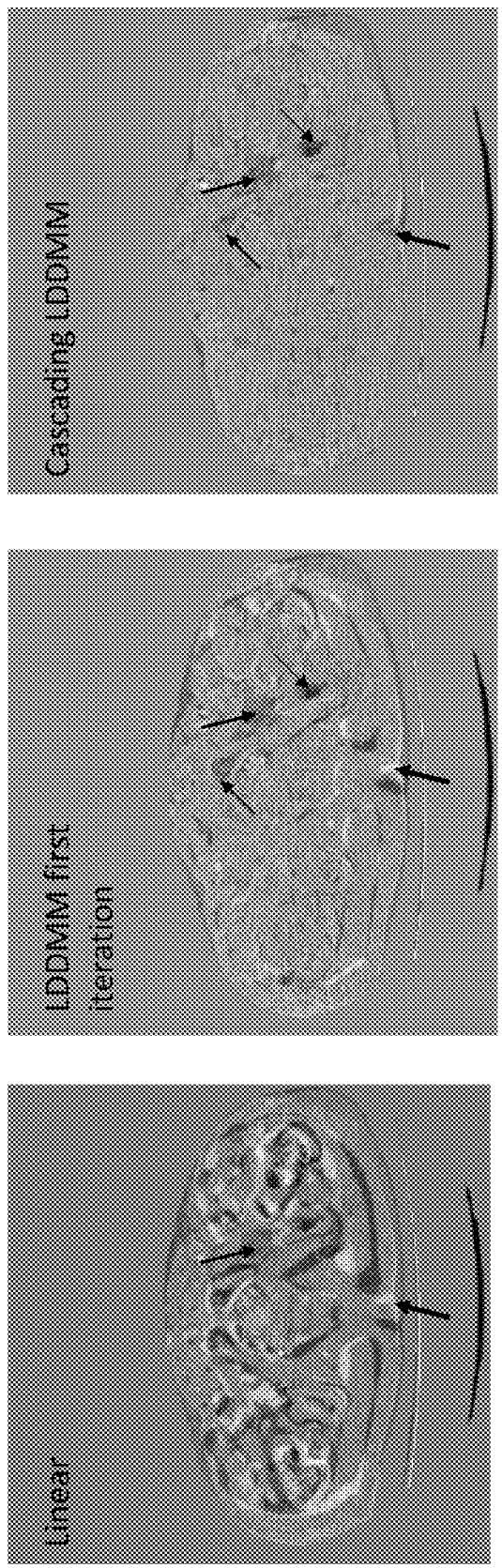
FIG. 8B shows the subtraction images by registering the CT image at the first time point to the CT image at the second time point by a linear, LDDMM, and cascading LDDMM transformation.

FIG. 8B shows the subtraction images by registering the CT image at the first time point to the CT image at the second time point by a linear, LDDMM, and cascading LDDMM transformation, respectively. The subtraction images clearly shows misaligned structures (indicated by bold black arrows)

as well as intensity changes in the muscle (indicated by white arrows) and the bone marrow (indicated by black arrows).

Figure 9:
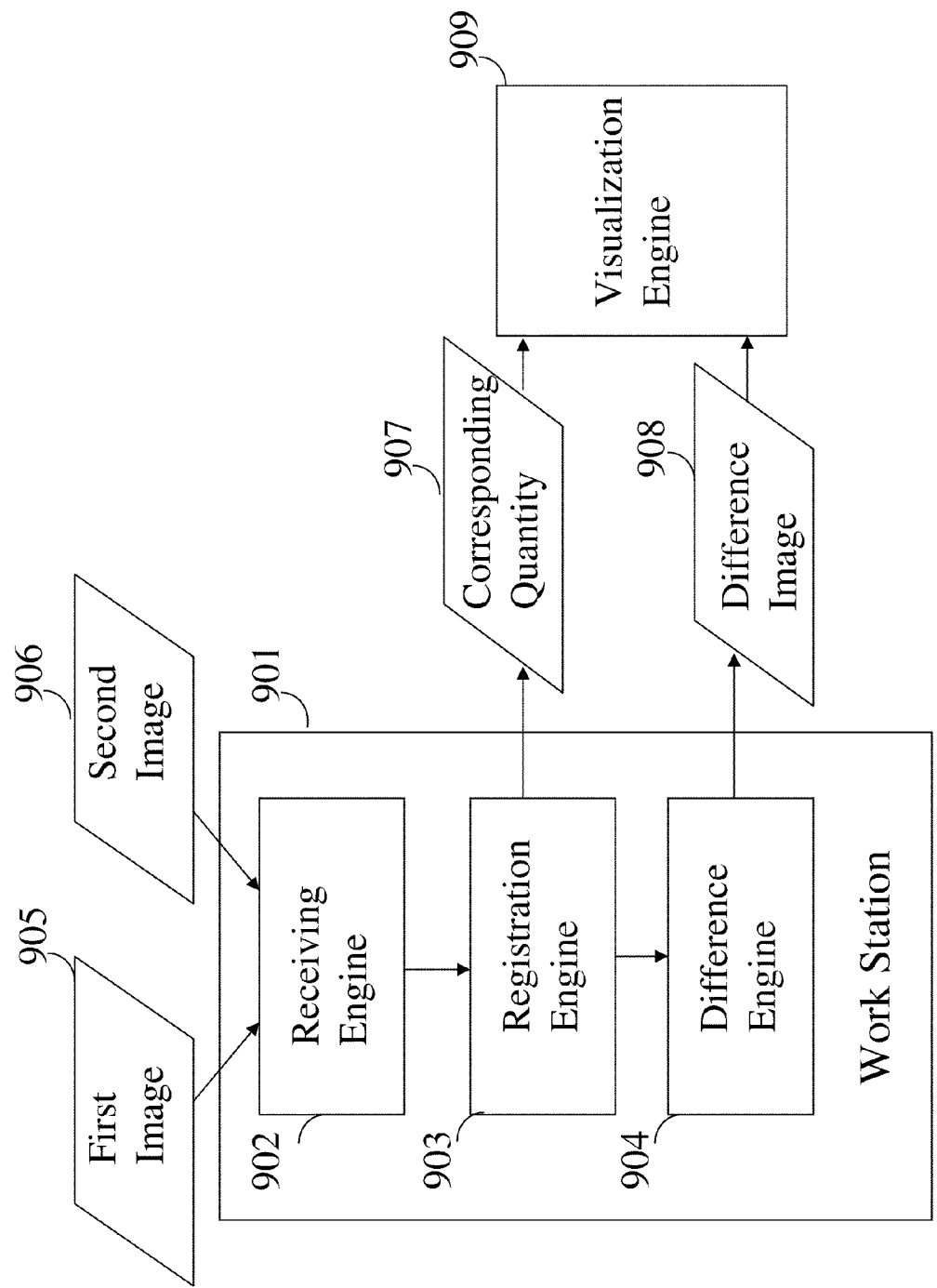
FIG. 9 depicts the operation of a workstation according to some embodiments of the current invention.

FIG. 9 depicts the operation of a workstation 901 according to some embodiments of the current invention. Workstation 901 includes receiving engine 902, registration engine 903, and difference engine 904.

Receiving engine 902 may, for example, receive first image 905 from, for example, data storage 108, and second image 906 from, for example, non-invasive medical imaging system 100. The first image 905 and second image 906 include a common tissue region from the same subject. The first image 905 may be obtained at an earlier time than the second image 906.

Registration engine 903 may perform a transformation in a space of diffeomorphism using, for example, large deformation diffeomorphic metric mapping (LDDMM), to register the first image to the second image. The registration engine may generate a corresponding quantity 907 which indicates the spatial effects of the transformation.

Difference engine 904 may further compute a difference between the registered first and second set of deformation patterns and output difference image 908. The computation may include a linear normalization process.

Workstation 901 may further comprise visualization engine 909 that receives the corresponding quantity 907 and the difference image 908. Visualization engine 909 may provide computer-aided detection and quantification of a pathology within the common tissue region on the first and second images 905 and 906 For example, a pre-existing segmentation of the tissue region on the first image 905 may be transferred and displayed on the second image 906 for a clinician to visually track the changes. For example, a portion of the difference image 908 may be displayed when the spatial effects characterized by the corresponding quantity 907 indicate an expansion.

Workstations 901 may be a computer with at least one central processing unit (CPU) and a plurality of memories. Workstations 901 may also be a dedicated processing machine with such devices as, for example, a field programmable gated array (FPGA), a digital signal processing (DSP) chip, a graphic processing unit (GPU), an application specific integrated circuit (ASIC), etc.

Receiving engine 902, registration engine 903, difference engine 904, and visualization engine 909 may be implemented by a computer with at least one central processing unit (CPU) and a plurality of memories. Receiving engine 902, registration engine 903, difference engine 904 may be implemented as, for example, a field programmable gated array (FPGA), a digital signal processing (DSP) chip, a graphic processing unit (GPU), an application specific integrated circuit (ASIC), etc. Visualization engine 909 may be implemented as, for example, a cathode ray tube (CRT) monitor, a liquid crystal display (LCD) monitor, a digital light projection (DLP) monitor, a plasma screen, an organic light emitting diode (OLED), etc.

In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A non-invasive medical imaging system, comprising:
an imaging scanner capable of generating an imaging signal from a subject under observation inside the imaging scanner;
a signal processing system in communication with said imaging scanner, and
a data storage unit in communication with said signal processing system,
   wherein said data storage unit is suitable for storing a first image corresponding to a tissue region of the subject,
   wherein said signal processing unit is capable of generating a second image encoding the tissue region of the subject by performing a reconstruction based on said imaging signal; said imaging signal acquired at a later time than the first image;
   wherein said signal processing system is constructed to receive the imaging signal from the imaging scanner and the first image from the data storage unit respectively,
   wherein said signal processing system is adapted to provide a registered first image by registering said first image to said second image via a transformation in a space of diffeomorphism,
   wherein said signal processing system is further adapted to compute a difference image between said second image and the registered first image; and
   wherein said signal processing system is further adapted to output said difference image.

2. The non-invasive medical imaging system of claim 1, wherein said imaging scanner is one of a magnetic resonance imaging (MRI) scanner, a computed tomography (CT) scanner, a positron emission tomography (PET) scanner, a single photo emission computed tomography (SPECT) scanner, or an ultrasound scanner.

3. The non-invasive medical imaging system of claim 1, wherein:
the signal processing system is further adapted to output a quantity corresponding to said transformation, said quantity indicating characteristic spatial effects of said transformation.

4. The non-invasive medical imaging system of claim 1, wherein the signal processing system further comprises at least one of a printing device, a display terminal, or another the data storage unit.

5. A workstation, comprising:
a receiving engine constructed to receive a first image and a second image of a subject;
a registration engine constructed to provide a registered first image by registering said first image to said second image via a transformation in a space of diffeomorphism, said transformation having a corresponding quantity representing characteristic spatial effects of the transformation; and
a difference engine constructed to compute a difference image between said second image and the registered first image of the subject.

6. The workstation engine of claim 5, further comprising:
a visualization engine constructed to provide a detection of a pathology of said subject based on at least one of the corresponding quantify and the difference image.

7. The workstation engine of claim 5, further comprising:
a visualization engine constructed to provide a quantification of a pathology of said subject based on said transformation.

8. A method for automatically tracking a time-dependent tissue change, comprising:
- obtaining a first radiographic image of a subject under observation;
- obtaining a second radiographic image of the subject at a later time;
    - wherein the first and second radiographic images comprise a common region of interest of said subject;
- providing a registered first radiographic image by registering the first radiographic image to the second image via a transformation in a space of diffeomorphism,
    - wherein said transformation has a corresponding quantity indicating characteristic spatial effects of said transformation;
- obtaining a difference image between the second radiographic image and the registered first radiographic image; and
- outputting both the corresponding quantity and the difference image,
    - wherein at least one of the difference image and the corresponding quantity characterizes the time-dependent tissue change being tracked.

9. The method of claim 8, wherein the radiographic image is at least one of a CT image, an MRI image, a PET image, a SPECT image, or an ultrasound image.

10. The method of claim 8, wherein the radiographic image is a three-dimensional image.

11. The method of claim 8, wherein the transformation is a large deformation diffeomorphic transform (LDDMM).

12. The method of claim 11, wherein a parameter controls a smoothness of said transformation.

13. The method of claim 12, wherein said transformation is repeated with said parameter decreased.

14. The method of claim 11,
wherein a differential operator is defined $L=-\alpha\nabla^2+\gamma I_{3\times 3}$,
wherein $I_{3\times 3}$ is an identity operator with a corresponding coefficient of $\alpha$, and $\nabla^2$ is an Laplacian operator with a corresponding coefficient of $\gamma$, and
wherein said parameter is determined by a ratio of $\alpha/\gamma$.

15. The method of claim 8, where in the corresponding quantity is a Jacobian matrix of the transformation.

16. The method of claim 8, wherein the difference image is normalized.

17. The method of claim 8, further comprising:
- segmenting the first radiographic image to generate a binary mask;
- transferring the binary mask to the second radiographic image via said transformation.

18. The method of 17, further comprising:
- calculating a first volume prescribed by the binary mask on said first radiographic image; and
- calculating a second volume prescribed by the transferred binary mask on the second radiographic image.

19. The method of claim 8, further comprising:
- inspecting both the corresponding quantity and the difference image; and
- identifying a pathology within said region of interest of said subject under observation.

20. A non-transitory computer readable medium, comprising software, when executed, causes a computer to execute the method according to claim 8.

* * * * *